(12) United States Patent
Vanderploeg et al.

(10) Patent No.: US 10,130,678 B2
(45) Date of Patent: Nov. 20, 2018

(54) SYSTEMS AND METHODS FOR IMPROVED DELIVERY OF OSTEOINDUCTIVE MOLECULES IN BONE REPAIR

(71) Applicant: BIOVENTUS, LLC, Durham, NC (US)

(72) Inventors: Eric Vanderploeg, Stoneham, MA (US); Howard Seeherman, Cambridge, MA (US); Christopher G. Wilson, Auburndale, MA (US); John Wozney, Hudson, MA (US); Christopher T. Brown, Chelmsford, MA (US); John A. Kambouris, Durham, NC (US)

(73) Assignee: Bioventus, LLC., Durham, NC (US)

( * ) Notice: Subject to any disclaimer, the term of this patent is extended or adjusted under 35 U.S.C. 154(b) by 12 days.

(21) Appl. No.: 14/983,008

(22) Filed: Dec. 29, 2015

(65) Prior Publication Data
US 2016/0184390 A1    Jun. 30, 2016

Related U.S. Application Data

(60) Provisional application No. 62/097,363, filed on Dec. 29, 2014, provisional application No. 62/144,276, filed on Apr. 7, 2015, provisional application No. 62/182,301, filed on Jun. 19, 2015.

(51) Int. Cl.
| | |
|---|---|
| *A61L 24/00* | (2006.01) |
| *A61L 27/12* | (2006.01) |
| *A61K 38/17* | (2006.01) |
| *A61K 33/06* | (2006.01) |
| *A61L 27/44* | (2006.01) |
| *A61L 27/54* | (2006.01) |
| *A61L 27/56* | (2006.01) |
| *A61K 38/18* | (2006.01) |
| *A61L 24/02* | (2006.01) |

(52) U.S. Cl.
CPC .............. *A61K 38/17* (2013.01); *A61K 33/06* (2013.01); *A61K 38/1875* (2013.01); *A61L 24/0015* (2013.01); *A61L 24/0036* (2013.01); *A61L 24/0084* (2013.01); *A61L 24/02* (2013.01); *A61L 27/12* (2013.01); *A61L 27/446* (2013.01); *A61L 27/54* (2013.01); *A61L 27/56* (2013.01); *A61L 2300/414* (2013.01); *A61L 2430/02* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 4,394,370 A * | 7/1983 | Jefferies | A61L 27/227 |
| | | | 106/122 |
| 5,385,887 A * | 1/1995 | Yim | A61K 38/1875 |
| | | | 106/645 |
| 5,422,340 A | 6/1995 | Ammann | |
| 5,631,142 A | 5/1997 | Wang | |
| 5,866,364 A | 2/1999 | Israel et al. | |
| 5,935,594 A | 8/1999 | Ringeisen et al. | |
| 5,948,428 A | 9/1999 | Lee et al. | |
| 6,027,743 A | 2/2000 | Khouri et al. | |
| 6,048,964 A | 4/2000 | Lee et al. | |
| 6,214,049 B1 | 4/2001 | Gayer et al. | |
| 6,221,111 B1 | 4/2001 | Piveteau et al. | |
| 6,281,195 B1 | 8/2001 | Rueger et al. | |
| 6,398,811 B1 | 6/2002 | McKay | |
| 6,425,949 B1 | 7/2002 | Lemaitre et al. | |
| 6,426,332 B1 | 7/2002 | Rueger et al. | |
| 6,551,995 B1 | 4/2003 | Oppermann et al. | |
| 6,586,388 B2 | 7/2003 | Oppermann et al. | |
| 6,642,285 B1 | 11/2003 | Bohner | |
| 6,677,432 B1 | 1/2004 | Oppermann et al. | |
| 6,733,562 B2 | 5/2004 | Bohner et al. | |
| 6,846,906 B1 | 1/2005 | Opperman et al. | |
| 6,949,251 B2 | 9/2005 | Dalal et al. | |
| 6,974,862 B2 | 12/2005 | Ringeisen et al. | |
| 6,979,735 B1 | 12/2005 | Booij et al. | |
| 7,049,348 B2 | 5/2006 | Evans et al. | |
| 7,122,253 B2 | 10/2006 | Yamaguchi et al. | |
| 7,156,860 B2 | 1/2007 | Evans et al. | |
| 7,166,133 B2 | 1/2007 | Evans et al. | |
| 7,214,765 B2 | 5/2007 | Ringeisen et al. | |
| 7,225,518 B2 | 6/2007 | Eidenschink et al. | |
| 7,235,107 B2 | 6/2007 | Evans et al. | |
| 7,241,316 B2 | 7/2007 | Evans et al. | |
| 7,284,401 B2 | 10/2007 | Larson et al. | |

(Continued)

FOREIGN PATENT DOCUMENTS

| | | | |
|---|---|---|---|
| CN | 103357070 A | 10/2013 | |
| CN | 104127913 A | 11/2014 | |

(Continued)

OTHER PUBLICATIONS

International Search Report & Written Opinion; Appln No. PCT/US2015/067891; dated Mar. 16, 2016.
U.S. Appl. No. 15/339,834, filed Oct. 31, 2016, Eric Vanderploeg.
U.S. Appl. No. 14/839,786, filed Aug. 28, 2015, Christopher G. Wilson.
U.S. Appl. No. 15/589,005, filed May 8, 2017, Orly Grinberg.
U.S. Appl. No. 15/619,767, filed Jun. 12, 2017, Jeffrey Welch.

(Continued)

*Primary Examiner* — Dennis J Parad
(74) *Attorney, Agent, or Firm* — Kacvinsky Daisak Bluni PLLC; Judith Toffenetti

(57) ABSTRACT

Systems and methods for preparing synthetic osteoinductive bone grafts are provided in which a porous ceramic granule, which may be incorporated within a biocompatible matrix material, is loaded with an osteoinductive agent. Loading of granules is facilitated in some cases by the use of low-pH buffers and pre-treatments.

12 Claims, 13 Drawing Sheets

(56) References Cited

U.S. PATENT DOCUMENTS

| | | |
|---|---|---|
| 7,318,840 B2 | 1/2008 | McKay |
| 7,357,941 B2 | 4/2008 | Dalal et al. |
| 7,390,498 B2 | 6/2008 | Dalal et al. |
| 7,393,405 B2 | 7/2008 | Bohner |
| 7,410,947 B2 | 8/2008 | Rueger et al. |
| 7,413,753 B2 | 8/2008 | Li et al. |
| 7,435,262 B2 | 10/2008 | Michelson |
| 7,504,374 B2 | 3/2009 | Marx et al. |
| 7,520,888 B2 | 4/2009 | Trieu |
| 7,563,455 B2 | 7/2009 | McKay |
| 7,598,219 B2 | 10/2009 | Zanella et al. |
| 7,611,536 B2 | 11/2009 | Michelson |
| 7,670,419 B2 | 3/2010 | Bohner |
| 7,671,014 B2 | 3/2010 | Beals et al. |
| 7,722,895 B1 | 5/2010 | McKay et al. |
| 7,723,291 B2 | 5/2010 | Beals et al. |
| 7,723,395 B2 | 5/2010 | Ringeisen et al. |
| 7,744,651 B2 | 6/2010 | Trieu et al. |
| 7,749,268 B2 | 7/2010 | Trieu |
| 7,749,964 B2 | 7/2010 | Zhang et al. |
| 7,776,100 B2 | 8/2010 | Brekke et al. |
| 7,803,369 B2 | 9/2010 | Vukicevic et al. |
| 7,806,911 B2 | 10/2010 | Peckham |
| 7,833,270 B2 | 11/2010 | McKay |
| 7,833,278 B2 | 11/2010 | Evans et al. |
| 7,842,669 B2 | 11/2010 | Zhang et al. |
| 7,887,598 B2 | 2/2011 | Evans et al. |
| 7,892,291 B2 | 2/2011 | Evans et al. |
| 7,892,532 B2 | 2/2011 | Titus et al. |
| 7,910,552 B2 | 3/2011 | Birr et al. |
| 7,910,690 B2 | 3/2011 | Ringeisen et al. |
| 7,923,432 B2 | 4/2011 | McKay |
| 7,939,092 B2 | 5/2011 | McKay et al. |
| 7,964,208 B2 | 6/2011 | Spagnoli et al. |
| 7,981,156 B2 | 7/2011 | Pafford et al. |
| 8,012,139 B2 | 9/2011 | McKay et al. |
| 8,012,192 B2 | 9/2011 | Eidenschink et al. |
| 8,039,433 B2 | 10/2011 | McKay |
| 8,048,857 B2 | 11/2011 | McKay et al. |
| 8,080,521 B2 | 12/2011 | Beals et al. |
| 8,092,452 B2 | 1/2012 | Stamps et al. |
| 8,092,464 B2 | 1/2012 | McKay |
| 8,092,541 B2 | 1/2012 | Peckham |
| 8,092,823 B2 | 1/2012 | McKay et al. |
| 8,101,676 B2 | 1/2012 | McKay |
| 8,105,383 B2 | 1/2012 | Michelson |
| 8,119,591 B2 | 2/2012 | Vukicevic et al. |
| 8,133,500 B2 | 3/2012 | Ringelsen et al. |
| 8,137,403 B2 | 3/2012 | Michelson |
| 8,147,495 B2 | 4/2012 | McKay |
| 8,147,862 B2 | 4/2012 | McKay |
| 8,148,326 B2 | 4/2012 | Beals et al. |
| 8,148,329 B2 | 4/2012 | McKay et al. |
| 8,162,992 B2 | 4/2012 | McKay |
| 8,163,018 B2 | 4/2012 | Trieu |
| 8,163,032 B2 | 4/2012 | Evans et al. |
| 8,163,033 B2 | 4/2012 | Luqinbuehl |
| 8,188,038 B2 | 5/2012 | McKay |
| 8,197,840 B2 | 6/2012 | Vukicevic et al. |
| 8,198,237 B2 | 6/2012 | Ron |
| 8,206,457 B2 | 6/2012 | Luqinbuehl et al. |
| 8,226,729 B2 | 7/2012 | McKay |
| 8,287,641 B2 | 10/2012 | Bohner |
| 8,343,221 B2 | 1/2013 | Trieu |
| 8,377,136 B2 | 2/2013 | Simonton |
| 8,383,092 B2 | 2/2013 | Lee et al. |
| 8,388,626 B2 | 3/2013 | Peckham |
| 8,389,588 B2 | 3/2013 | Ringeisen et al. |
| 8,399,010 B2 | 3/2013 | McKay |
| 8,399,619 B2 | 3/2013 | Trieu et al. |
| 8,431,147 B2 | 4/2013 | Drapeau et al. |
| 8,431,148 B2 | 4/2013 | McKay |
| 8,449,622 B2 | 5/2013 | McKay |
| 8,470,354 B2 | 6/2013 | McKay et al. |
| 8,475,824 B2 | 7/2013 | McKay |
| 8,506,983 B2 | 8/2013 | Mohan et al. |
| 8,507,008 B2 | 8/2013 | Li et al. |
| 8,524,265 B2 | 9/2013 | McKay |
| 8,529,533 B2 | 9/2013 | Amsden et al. |
| 8,551,514 B2 | 10/2013 | Ringelsen et al. |
| 8,574,611 B2 | 11/2013 | Seibl et al. |
| 8,603,184 B2 | 12/2013 | Rizzoli et al. |
| 8,617,252 B2 | 12/2013 | McKay |
| 8,623,094 B2 | 1/2014 | Evans et al. |
| 8,633,299 B2 | 1/2014 | Ringeisen et al. |
| 8,653,029 B2 | 2/2014 | Vickers et al. |
| 8,658,217 B2 | 2/2014 | McKay et al. |
| 8,658,917 B2 | 2/2014 | Westhues |
| 8,663,672 B2 | 3/2014 | Manrique et al. |
| 8,697,107 B2 | 4/2014 | Drapeau et al. |
| 8,697,108 B2 | 4/2014 | Ringeisen et al. |
| 8,728,509 B2 | 5/2014 | McKay |
| 8,734,835 B2 | 5/2014 | McKay et al. |
| 8,840,618 B2 | 9/2014 | Trieu et al. |
| 8,840,913 B2 | 9/2014 | McKay et al. |
| 2005/0119761 A1* | 6/2005 | Matsumoto ............. A61L 27/12 623/23.56 |
| 2008/0206308 A1 | 8/2008 | Jabbari |
| 2009/0142385 A1 | 6/2009 | Gross et al. |
| 2009/0220475 A1 | 9/2009 | Bohner et al. |
| 2009/0248162 A1 | 10/2009 | Peckham |
| 2010/0191292 A1 | 7/2010 | DeMeo et al. |
| 2010/0221777 A1 | 9/2010 | Choe et al. |
| 2010/0248368 A1 | 9/2010 | Lynn |
| 2011/0165215 A1 | 7/2011 | McKay et al. |
| 2012/0016390 A1 | 1/2012 | Lee et al. |
| 2012/0029559 A1 | 2/2012 | Lee et al. |
| 2012/0109314 A1 | 5/2012 | Peckham |
| 2012/0141557 A1 | 6/2012 | McKay |
| 2012/0149849 A1 | 6/2012 | Dalsin et al. |
| 2012/0179083 A1 | 7/2012 | Lee et al. |
| 2012/0219599 A1 | 8/2012 | Hans Moore et al. |
| 2012/0237586 A1 | 9/2012 | Okamoto |
| 2012/0330436 A1 | 12/2012 | Bohner et al. |
| 2013/0053850 A1 | 2/2013 | DeMeo et al. |
| 2013/0149294 A1 | 6/2013 | Rueger et al. |
| 2013/0149348 A1 | 6/2013 | De Groot et al. |
| 2013/0184835 A1 | 7/2013 | Ferrari |
| 2013/0190236 A1 | 7/2013 | Patterson et al. |
| 2013/0195928 A1 | 8/2013 | Lamberti |
| 2013/0287817 A1 | 10/2013 | Drapeau et al. |
| 2013/0325126 A1 | 12/2013 | Bradica et al. |
| 2014/0093571 A1 | 4/2014 | Rizzoli et al. |
| 2014/0107593 A1 | 4/2014 | Gao et al. |
| 2014/0200182 A1 | 7/2014 | Ron |

FOREIGN PATENT DOCUMENTS

| | | |
|---|---|---|
| CN | 104353121 A | 2/2015 |
| EP | 1216718 A1 | 6/2002 |
| EP | 1344538 A1 | 9/2003 |
| JP | 2003-518411 A | 6/2003 |
| JP | 2009-512517 A | 3/2009 |
| JP | 2009-528080 A | 8/2009 |
| JP | 2013-540465 A | 11/2013 |
| JP | 2013-545584 A | 12/2013 |
| WO | 9507108 A2 | 3/1995 |
| WO | 2002087475 A1 | 11/2002 |
| WO | 2005014072 A1 | 2/2005 |
| WO | 2006082442 A1 | 8/2006 |
| WO | 2007097710 A1 | 8/2007 |
| WO | 2012028620 A1 | 3/2012 |
| WO | 2012082773 A1 | 6/2012 |
| WO | 2013152418 A1 | 10/2013 |
| WO | 2016109555 A1 | 7/2016 |

OTHER PUBLICATIONS

International Search Report & Written Opinion; Appln No. PCT/US2016/059782, dated Feb. 3, 2017, 9 pages.

International Search Report & Written Opinion; Appln No. PCT/US2015/047571, dated Dec. 7, 2015, 9 pages.

Liu et al., Polym. Sci., 2015, vol. 1(1): 1-6.

(56) References Cited

OTHER PUBLICATIONS

Montufar et al., J. Mater. Sci. Mater. Med., 2010, vol. 21: 863-869.
International Search Report & Written Opinion; Appln No. PCT/US2017/031584, dated Aug. 14, 2017, 11 pages.
International Search Report & Written Opinion; Appln No. PCT/US2017/036979, dated Aug. 18, 2017, 12 pages.

\* cited by examiner

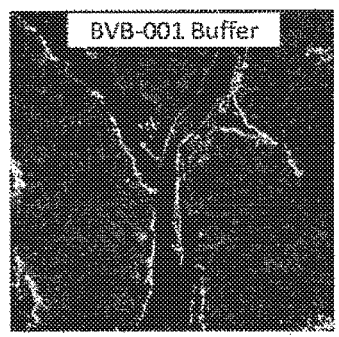
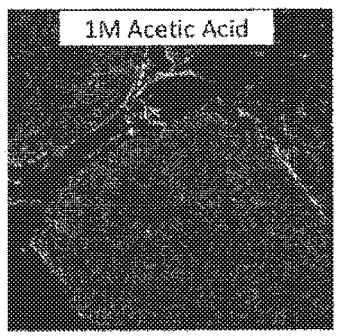
FIG. 9A          FIG. 9B
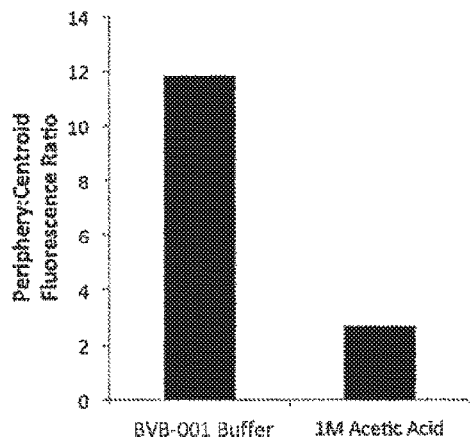
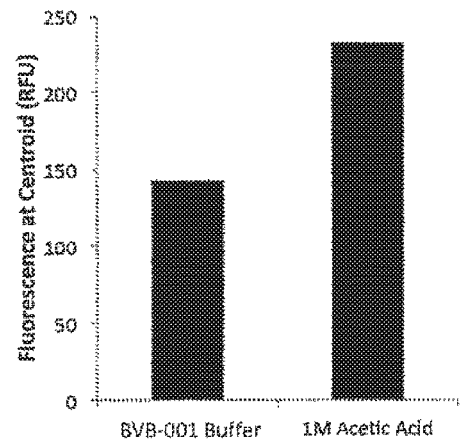
FIG. 9C          FIG. 9D

SYSTEMS AND METHODS FOR IMPROVED DELIVERY OF OSTEOINDUCTIVE MOLECULES IN BONE REPAIR

CROSS-REFERENCE TO RELATED APPLICATIONS

This application claims the benefit of priority under 35 U.S.C. § 119(e) to (i) U.S. Provisional Patent Application No. 62/097,363 by Vanderploeg et al., filed Dec. 29, 2014, (ii) U.S. Provisional Patent Application No. 62/144,276 by Wilson et al., Apr. 7, 2015, and (iii) U.S. Provisional Patent Application No. 62/182,301 by Vanderploeg et al., filed Jun. 19, 2015. The entire disclosure of each of the foregoing applications is incorporated by reference for all purposes herein.

FIELD OF THE INVENTION

This application relates to medical devices and biologic therapies, and more particularly to bone cements, bone putties and granule-binder composites.

BACKGROUND

Bone grafts are used in roughly two million orthopedic procedures each year, and generally take one of three forms. Autografts, which typically consist of bone harvested from one site in a patient to be grafted to another site in the same patient, are the benchmark for bone grafting materials, inasmuch as these materials are simultaneously osteoconductive (serving as a scaffold for new bone growth), osteoinductive (promoting the development of osteoblasts) and osteogenic (containing osteoblasts which form new bone). However, limitations on the supply of autografts have necessitated the use of cadaver-derived allografts. While they are more available that autografts, allografts may trigger host-graft immune responses or may transmit infectious or prion diseases, and are often sterilized or treated to remove cells, eliminating their osteogenicity.

The shortcomings of human-derived bone graft materials have fed a growing interest in synthetic bone graft materials, which typically comprise calcium ceramics and/or cements delivered as pastes or putties. These materials are osteoconductive, but not osteoinductive or osteogenic. To improve their efficacy, synthetic calcium-containing materials have been loaded with osteoinductive materials, particularly bone morphogenetic proteins (BMPs), such as BMP-2, BMP-7, or other growth factors such as fibroblast growth factor (FGF), insulin-like growth factor (IGF), platelet-derived growth factor (PDGF), and/or transforming growth factor beta (TGF-ß). However, significant technical challenges have prevented the efficient incorporation of osteoinductive materials into synthetic bone graft substitutes which, in turn, has limited the development of high-quality osteoinductive synthetic bone graft materials.

One challenge has been the development of a graft matrix which delivers an osteoinductive material over time, rather than in a single short burst release, and which has appropriate physical characteristics to support new bone growth. The production of a material with appropriate physical characteristics involves balancing several competing needs: the ideal materials should be rigid enough to bear loads applied to the graft during and after implantation; they should have sufficient porosity to allow for cell and tissue infiltration; they should degrade or dissolve at a rate which permits its replacement by new bone; and they should elute osteoinductive material in a temporal and spatial manner that is appropriate for bone generation. An optimal graft matrix, which meets each of these design criteria, has not yet been realized, and BMP-eluting synthetic bone grafts currently available commercially do not meet these requirements. Accordingly, need exists for a synthetic bone graft material which reconciles these competing needs and which provides optimal release of osteoinductive materials, particularly BMPs.

SUMMARY OF THE INVENTION

The present invention addresses an important unmet need in the field by providing synthetic bone graft materials with improved elution of osteoinductive proteins in combination with optimal physical characteristics, as well as methods of making and using the same. In one aspect, the present invention relates to a composition that includes a calcium ceramic granule, an osteoinductive protein, and a biocompatible matrix. The calcium ceramic granule, which is disposed within the biocompatible matrix, includes at least one macropore and at least one micropore, and has a specific surface area greater than about 30 $m^2/g$. In some cases, the composition includes a plurality of calcium ceramic granules with mean cross-sectional dimensions in one of the following ranges: 80-250 microns, 90-425 microns, 425-800 microns, and 1-2 mm. In various cases, the at least one macropore has a cross-sectional dimension of between 40 and 100 microns, the at least one micropore has a cross-sectional dimension of approximately 10 microns, and/or the osteoinductive protein is adsorbed to a surface of the granule within the at least one micropore. And in some cases at least 50% of the osteoinductive protein is retained in the at least one calcium ceramic granule after an interval of seven days to fourteen days post implantation.

In another aspect, the invention relates to a calcium granule itself, which granule includes at least one macropore and at least one micropore and has a specific surface area of about 50 to about 80 $m^2/g$. The granule also includes one or more of the following features: the granule has a cross-sectional dimension of between about 80 and about 1000 microns, and the at least one macropore has a cross-sectional dimension of between about 20 and about 50 microns, and/or the at least one micropore has a cross-sectional dimension of approximately 10 microns, and/or an osteoinductive protein is adsorbed to a surface of the granule within the at least one micropore; at least 50% of the osteoinductive protein, in turn, is optionally retained in the granule after intervals of seven to fourteen days post implantation.

In another aspect, the present invention relates to a composition that includes a preformed calcium ceramic granule with a specific surface area greater than 30 $m^2/g$, which granule has an interconnected network of micropores defining at least one surface on the interior of the granule, and an osteoinductive protein associated with that at least one surface such that the protein is distributed on a portion of the at least one interior surface that is near the centroid of the granule as well as a portion of the interior surface near the exterior of the granule. For example, in some cases, the concentration of the osteoinductive protein on an interior surface near the centroid (i.e. within a radius of approximately 20% or, in some cases, 10% of the average distance from the centroid to the outer surface) can be at least 33% of the concentration of the protein found on the outer surface of the granule (e.g. a ratio of the concentration of protein on the surface to concentration near the centroid can be less than 3). In other embodiments, the concentration of the protein near the centroid is at least 12%, 15%, 20%, 25%, 30%, 40%, 50%, 60%, 70%, or 80% of the concentration on the exterior surface. Framed slightly differently, the ratio of concentration on the surface to concentration near the centroid may be 8:1, 7:1, 6:1, 5:1, 4:1, 3:1, 2:1 or even approximately 1:1 in various instances.

The composition according to this aspect of the invention can be obtained by a process that includes a step of contacting the granule with a first solution having a pH less than 4.5 and comprising the osteoinductive protein and a buffering agent having a pKa between 2.3 and 4.5. In some cases, the first solution has a pH of about 4 and consists essentially of the osteoinductive protein, 5 mM glutamic acid, 0.15 wt % glycine, 1 wt % sucrose, and sterile water for injection. In other cases, the first solution has a pH of about 3.5 and consists essentially of the osteoinductive protein, 25 mM glutamic acid, 0.75 wt % glycine, 1 wt % sucrose, and sterile water for injection. In still other cases, the first solution has a pH of about 4 and consists essentially of the osteoinductive protein, 25 mM glutamic acid, 2 wt % glycine, 1 wt % sucrose, and sterile water for injection. More generally, the buffering agent may be one or more of glycine, lactic acid, acetic acid, formic acid, malic acid, malonic acid, glutamic acid, aspartic acid, citric acid, tartaric acid, phosphoric acid, fumaric acid and succinic acid. In some cases, the granule has a pH of less than 7 prior to contacting the first solution. The process facilitates the distribution of the osteoinductive protein along inner and exterior surfaces of the granule described above.

In another aspect, the invention relates to a method of treating a patient that includes a step of contacting a bony tissue of the patient with a composition that includes (a) calcium ceramic granule having a specific surface area greater than 30 m$^2$/g and having an interconnected network of micropores defining at least one surface on an interior of the granule and (b) an osteoinductive protein associated with the at least one interior surface and distributed on a portion of the interior surface near the centroid of the granule and on an interior surface near the exterior of the granule. The bony tissue is optionally a site of a traumatic injury to the bone and/or a vertebra. The composition may include a biocompatible matrix (optionally containing collagen), in which case the ceramic granule is disposed within the matrix. The concentration of osteoinductive protein near the centroid is, in preferred cases (but not necessarily in all cases) at least 33% of the concentration of the protein found on the outer surface of the granule (e.g. a ratio of the concentration of protein on the surface to concentration near the centroid can be less than 3). In other instances, the concentration of the protein near the centroid is at least 12%, 15%, 20%, 25%, 30%, 40%, 50%, 60%, 70%, or 80% of the concentration on the exterior surface. Framed slightly differently, the ratio of concentration on the surface to concentration near the centroid may be 8:1, 7:1, 6:1, 5:1, 4:1, 3:1, 2:1 or even approximately 1:1 in various instances In yet another aspect, the present invention relates to a composition that includes a porous polymer matrix (optionally comprising collagen), a calcium ceramic granule contacting (e.g. embedded, partially embedded, and/or applied to the surface of) the porous polymer matrix, the calcium ceramic granule having a specific surface area greater than 30 m$^2$/g and having an interconnected network of micropores defining at least one surface on an interior of the granule, and an osteoinductive protein associated with the at least one interior surface such that a concentration of the osteoinductive protein is substantially the same on an interior surface near a centroid of the granule and on an interior surface near an exterior of the granule. In some instances, the matrix is a sponge having a plurality of pores, the pores having an average diameter of about 150 to about 300 microns. Alternatively or additionally, the osteoinductive protein is associated with the at least one interior surface of the granule by a method including the step of contacting the granule with a first solution comprising the osteoinductive protein and a buffering agent having a pKa between 2.3 and 4.5, the solution having a pH less than 4.5. The concentration of osteoinductive protein near the centroid is, in preferred cases (but not necessarily in all cases) at least 33% of the concentration of the protein found on the outer surface of the granule (e.g. a ratio of the concentration of protein on the surface to concentration near the centroid can be less than 3). In other instances, the concentration of the protein near the centroid is at least 12%, 15%, 20%, 25%, 30%, 40%, 50%, 60%, 70%, or 80% of the concentration on the exterior surface. Framed slightly differently, the ratio of concentration on the surface to concentration near the centroid may be 8:1, 7:1, 6:1, 5:1, 4:1, 3:1, 2:1 or even approximately 1:1 in various instances.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted. It will be understood that the invention is not necessarily limited to the particular embodiments illustrated herein.

FIGS. 9A and 9B show fluorescent micrographs of granules loaded with fluorescently-labeled BMP protein. FIGS. 9C and 9D show quantification of the signal from fluorescently labeled BMP protein throughout the granules when delivered in a weak buffer (BVB-001 Buffer) or a strong buffer (1M Acetic Acid). FIGS. 9A and C demonstrate that in a weakly buffered system the vast majority of the BMP is confined near the exterior of the granules, whereas in a strongly buffered system the BMP is more uniformly distributed between both the centroid and the exterior. The ratio of peripheral to centroid fluorescence is lower (e.g. closer to 1:1) in the strong buffer with at least 30% of the total signal found in the centroid. FIG. 9D demonstrates that this is due, at least in part, to an increase in signal in the centroid of the granule.

FIGS. 13A-B show the structure of granules of the present invention demonstrating the interconnected pore structure via SEMs of the internal architecture (A) and the open surface architecture (B). FIG. 13C depicts fluoro-labeled BMP penetrating into the interior structure of the granules when delivered in a well buffered, pH 4 solution. FIG. 13D shows the BMP retention profile of preformed CaP granules of the present invention compared to BMP retention in a calcium phosphate cement, where the BMP is entirely trapped within the cement during the reaction. These data demonstrate that the present invention is able to mimic the BMP retention profile of a CaP cement by implementing the critical design features described herein.

DETAILED DESCRIPTION

Osteoinductive Compositions

Figure 1:
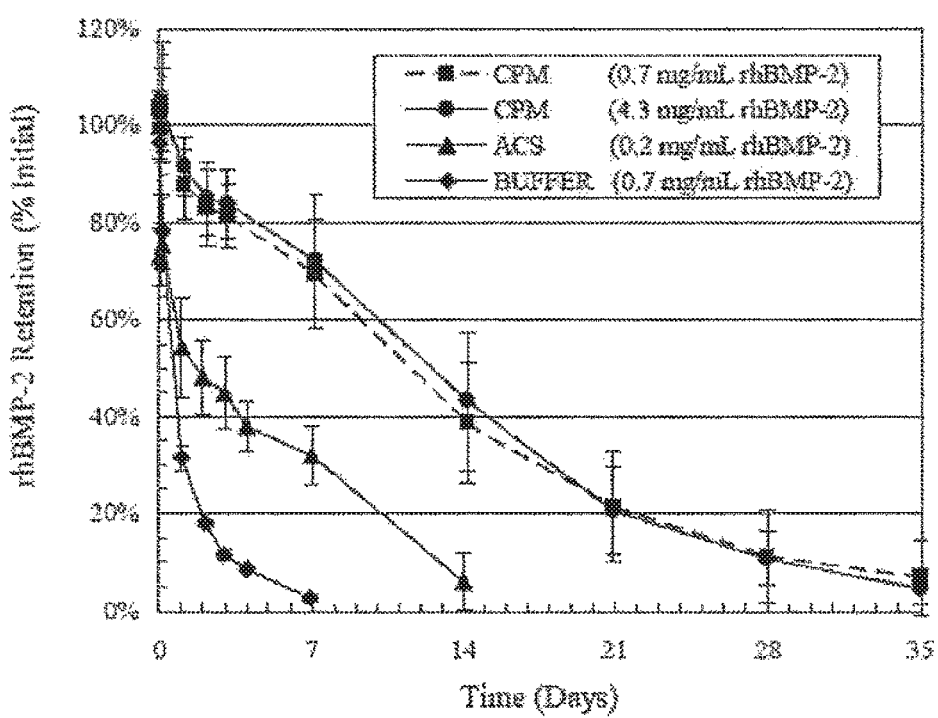
FIG. 1 shows in-situ retention of rhBMP-2 (% of initial dose, mean±SD) vs time (days) after injection with rhBMP-2/calcium phosphate matrix (CPM, 0.7 and 4.2 mg/mL) compared to 0.2 mg/mL rhBMP-2 delivered on an absorbable collagen sponge (ACS) and in buffer (0.7 mg/mL) in a rabbit ulna osteotomy model.
Figures 2A, 2B, 2C, 2D:
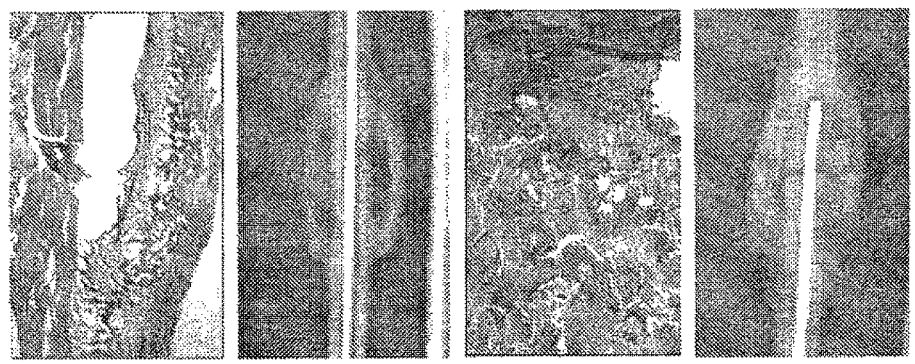
FIGS. 2A through 2D show a comparison of callus formation in a nonhuman primate fibula osteotomy model in response to treatment with BMP-2 delivered in an absorbable collagen sponge (ACS) compared to treatment with BMP-2 delivered in a granulating calcium phosphate matrix (CPM) at 8 weeks. The BMP-2/ACS-treated osteotomy shown in panels A and B has a hollow callus architecture resulting from bone formation outside the microporous ACS carrier rather than within the ACS carrier. In contrast the BMP-2/CPM-treated repair shown in panels C and D has a much more uniform callus architecture resulting from the slower BMP-2 release profile.

Synthetic bone grafts (also referred to interchangeably as "implants" or "constructs") utilizing the compositions of the invention generally include three components: an osteoconductive material, such as a calcium ceramic or other solid mineral body, an osteoinductive material such as a bone morphogenetic protein, and a biocompatible matrix such as a collagen sponge. As used herein, osteoconductive materials refer to any materials which facilitates the ingrowth or ongrowth of osteoblastic cells including osteoblasts, pre-osteoblasts, osteoprogenitor cells, mesenchymal stem cells and other cells which are capable of differentiating into or otherwise promoting the development of cells that synthesize and/or maintain skeletal tissue. In preferred embodiments of the present invention, the osteoconductive material is a granule comprising an osteoconductive calcium phosphate ceramic that is adapted to provide sustained release of an osteoinductive substance that is loaded onto the granule. In some cases, the granule includes interconnected, complex porous structures. Exemplary granules, which the inventors have found exhibit BMP binding and elution characteristics that are optimized for use in constructs, systems and methods of the present invention are described in International Patent Application Nos. PCT/CH2014/000085 and PCT/CH2015/000092 by Bohner et al. The entire disclosure of both of these applications is incorporated herein for all purposes.

The granules are generally made of any suitable osteoconductive material having a composition and architecture appropriate to allow an implant of the invention to remain in place and to release osteoinductive material over time intervals optimal for the formation and healing of bone (e.g. weeks or months). While these characteristics may vary between applications, the granules generally include, without limitation, monocalcium phosphate monohydrate, dicalcium phosphate, dicalcium phosphate dehydrate, octocalcium phosphate, precipitated hydroxyapatite, precipitated amorphous calcium phosphate, monocalcium phosphate, alpha-tricalcium phosphate (α-TCP), beta-tricalcium phosphate (ß-TCP), sintered hydroxyapatite, oxyapatite, tetracalcium phosphate, hydroxyapatite, calcium-deficient hydroxyapatite, and combinations thereof.

Osteoinductive materials generally include peptide and non-peptide growth factors that stimulate the generation of osteoblasts from populations of pre-cursor cells. In some embodiments, the osteoinductive material is a member of the transforming growth factor beta (TGF-ß) superfamily such as BMP-2, BMP-3, BMP-4, BMP-5, BMP-6, BMP-7, BMP-9, or a designer BMP such as the BMP-GER or BMP-GER-NR chimeric BMPs described in U.S. Pat. No. 8,952,131 by Berasi et al. entitled "Designer Osteogenic Proteins," the entire disclosure of which is hereby incorporated by reference for all purposes. In other embodiments, the osteoinductive material is a fibroblast growth factor, insulin-like growth factor, platelet-derived growth factor, a small molecule, a nucleotide, a lipid, or a combination of one or more of the factors listed herein.

The third component of implants (also referred to herein as "constructs") according to the present invention is the biocompatible matrix, which can be any suitable biocompatible material which (a) when used in concert with the granules, exhibits sufficient rigidity and/or column strength to withstand the loads placed upon it when implanted, (b) which does not cause excessive inflammation (i.e. inflammation sufficient to inhibit or prevent the formation of new bone or the healing of a broken bone), inhibit the proliferation of osteoblasts, or otherwise interfere with the activity of the granules and/or the osteoinductive material, and (c) has sufficient cohesion over an appropriate interval to permit the deposition of new bone within a defined area. In addition, the biocompatible matrix is optionally degradable and/or osteoconductive. The biocompatible matrix is, in various embodiments, hyaluronic acid (HA), and functionalized or modified versions thereof, collagen, whether animal or recombinant human, gelatin (animal or recombinant human), fibrin, chitosan, alginate, agarose, self-assembling peptides, whole blood, platelet-rich plasma, bone marrow aspirate, polyethylene glycol (PEG) and derivatives thereof, functionalized or otherwise cross-linkable synthetic biocompatible polymers including poly(lactide-co-glycolide), poly (caprolactone), poly(lactic acid), poly(glycolic acid), poloxamers and other thermosensitive or reverse-thermosensitive polymers known in the art, and copolymers or admixtures of any one or more of the foregoing.

Technical Considerations for Implant Design

Implants of the invention, which include the osteoinductive materials, granules and biocompatible matrices as described above, generally have characteristics which are tailored to the facilitation of bone growth and healing and which are not exhibited by currently available synthetic bone grafting materials. One important distinguishing characteristic of the implants described herein is that they retain and release osteoinductive materials over intervals sufficient to induce bone formation in humans.

BMPs induce bone formation primarily by stimulating differentiation of osteoblast progenitors either resident at the site of repair in the bone or in the surrounding soft tissue. Physiological bone repairs are stimulated by the release of picogram/femtogram amounts of BMPs stored in the mineral phase of bone and from newly synthesized BMPs secreted by bone progenitor cells at the site of the repair. These two sources in concert with negative regulators maintain BMP concentrations at the site of repair at physiological levels for the appropriate amount of time to induce a successful bone repair.

Exogenous BMPs are, ideally, delivered in constructs which elute BMP in amounts and over intervals that mimic the physiological BMP response. It should be noted, however, that the administration of much larger pharmacological BMP concentrations is generally required to achieve physiological concentrations of BMPs at the cellular level and to maintain the physiological concentrations for the appropriate amount of time. This is due to a combination of factors that are not totally understood. Without wishing to be bound by any theory, one factor driving the need for super-physiological BMP concentrations in these constructs may be the inability of exogenous BMP to mimic the efficiency of physiological local release of endogenous BMPs from bone and newly formed endogenous BMPs from cells. In addition, rhBMPs are generally insoluble at physiological pH, so (again, not wishing to be bound by any theory) much of the exogenously delivered BMP may not be biologically available.

The amount of exogenous rhBMP required to stimulate bone repair appears to be species dependent. Empirical data suggests that lower concentrations of exogenous rhBMPs are required to stimulate bone formation in small animals such as rodents and rabbits compared to larger animals including dogs, sheep and goats. Nonhuman primates and humans appear to require the highest concentrations of exogenous rhBMPs to stimulate bone repair. For example, the FDA approved concentration of rhBMP-2 delivered in an absorbable collagen sponge (ACS) for bone repair in dogs is 0.2 mg/mL compared to 1.5 mg/mL in people. Again, the factors contributing to this difference in required exogenous rhBMP concentration are not clearly understood, but those of skill in the art will understand that inter-species differences must be considered in evaluating findings in animal models for its applicability to human patients.

Similarly, the interval over which BMPs must be delivered to tissues varies among species: BMP residence time for repairs in rodents and rabbits can be as short as several days due to their rapid intrinsic rate of bone formation, while nonhuman primates and human patients generally requires several weeks BMP residence time. While not wishing to be bound by any theory, the longer interval observed in primates and humans appears to be related to the amount of time for the healing process to transition from an initial catabolic inflammatory phase caused by the surgery or trauma to an anabolic phase involving the migration and differentiation of osteoblast progenitors and associated new blood vessel units to support the fusion/repair process. Short BMP residence time optimal for rodents may not maintain physiological BMPs levels for a sufficient amount of time to stimulate bone repair in animals with slower bone formation rates. Conversely, BMP may not be released in sufficient amounts from a carrier with a longer retention profile to stimulate optimal bone formation in animals with rapid intrinsic bone formation rates.

As one example, the residence time of BMPs delivered locally in buffer solution to a repair site is extremely short, and even when relatively large amounts of BMP are delivered in solution, an adequate bone response is only stimulated in rodent models. For applications in non-human primates and human patients, an extended-release carrier is preferably used to localize BMP to sites of treatment for a period of weeks.

One strategy for providing extended local BMP release is to utilize carriers that mimic the binding of BMP to endogenous extracellular matrix. As one example, collagenous carriers exhibit longer BMP residence times than BMP solutions, due (without being bound to any theory) to the intrinsic binding properties of BMP to extracellular matrix components including endogenous collagen. Ceramic carriers including calcium phosphate matrices (CPM) can further extended the duration over which BMPs are released from the matrix. The release of BMP from ceramic carriers may require the same osteoclastic resorption observed in release of BMP from bone. Based on this unique property, implants comprising ceramic components embedded within composite carriers, as are used in the present invention, may be superior vehicles for BMP delivery compared to other naturally occurring and synthetic biomaterials.

In addition to efficacy considerations, controlling the release of BMPs from a carrier is also important for patient safety. With respect to the avoidance of trabecular bone resorption, the rapid release of BMP within metaphyseal bone or into the trabecular bone associated with interbody fusions where the endplates are penetrated results in rapid upregulation of osteoblast precursor cells in a location where there are also significant numbers of osteoclast precursor cells. As a result of normal cross talk between these two cell types, sufficient mature osteoclasts are generated to cause transient resorption of trabecular bone prior to bone formation. This phenomenon may be partially responsible for osteolysis sometimes observed when BMPs are used in interbody fusions and metaphyseal bone repairs.

Designing Granules for Optimal BMP Delivery

Previous experience with calcium phosphate cements demonstrated incorporation of BMP within the cement itself provides appropriate BMP retention (FIG. 1) for optimal bone formation in a variety of indications including segmental repair, diaphyseal repairs and metaphyseal repairs. However, calcium cement hardening is highly dependent on the conditions present during hardening, and the physical properties of hardened cements, such as porosity, etc, may vary significantly among individual applications. This variability prompted an investigation of other, more reliable carrier materials such as preformed calcium ceramic granules.

Without wishing to be bound by any theory, optimal BMP retention profiles observed using granules or other carriers of the present invention (FIG. 4 and FIG. 5), is in part the result of cell-based osteoclast resorption of BMP incorporated within the carrier material itself. When the carrier is a cement, BMP is incorporated within the cement by using a BMP solution to hydrate the cement powder precursors. During the cementing reaction BMP binds with a high affinity to the surfaces of the rapidly forming poorly crystalline hydroxyapatite and is trapped within the cement as well as on the cement surface. BMP is then gradually released, presumably in soluble form, by the low pH environment created by the osteoclasts during the cement resorption process. Osteoclasts have to completely resorb the cement to release all of the contained BMP.

In contrast, when BMP is added to currently available preformed calcium phosphate cement particles after the cementing reaction has occurred, it tends to concentrate on the outer surfaces of such particles. Consequently, BMP retention is significantly reduced (i.e. the release tends to be much faster) as osteoclasts can rapidly access and release almost all of the BMP without the need for significant granule resorption Relatedly, when BMP is incorporated into calcium cements, it is released more predictably and consistently than is observed when BMP is added to currently available CaP granules. Without wishing to be bound by any theory, it is believed that, again, the consistency of release from CaP cements is due in part to the involvement of osteoclast-mediated resorption in the release process. And again, the consistent release profiles observed in CaP cements is not easily replicated using preformed granules.

The target BMP retention profile for a BMP utilizing preformed CaP granules in people, based on previous studies evaluating rhBMP-2 delivered in a calcium phosphate matrix (CPM) discussed previously, requires minimal burst release in the first 24 hours, a half-life of approximately 1 week and a mean residence time of approximately 2 weeks. The ability of a preformed CaP granule composite carrier to deliver an optimal BMP retention profile is dependent on a number of parameters intrinsic to the granules. The BMP binding affinity of the CaP granules determines the rate of BMP binding and the in vitro/in vivo retention. BMP binding affinity is, in turn, dependent on the surface chemistry and the specific surface area (nanoscale roughness) of the granules. These parameters help define the degree to which BMP becomes associated with the surfaces of the granules, but are not sufficient to mimic the BMP retention and release kinetics observed in cements; the granule must also have an appropriate internal architecture. The ideal granule architecture incorporates both macropores (pores having diameters or cross-sectional dimensions of between 40 and 100 microns or so) and micropores (pores of approximately 10 microns in cross section), in a manner that (a) provides sufficient internal surface area to load the granules with BMP in quantities similar to those achievable in cements, while (b) permitting fluid infiltration of the granules to allow BMP in solution to access the internal pores surfaces of the granules and (c) does not reduce the compressive strength of the granules below the threshold required for their use in vivo. While currently available granules do not meet these criteria, in CaP granules which meet these requirements (as described below), BMP release profiles are in line with those observed in CaP cements, and release of BMP from such granules is thought (without wishing to be bound by theory) to be dependent on osteoclast resorption, as BMP associated with internal pore surfaces is not readily accessible to osteoclasts.

Figure 3:
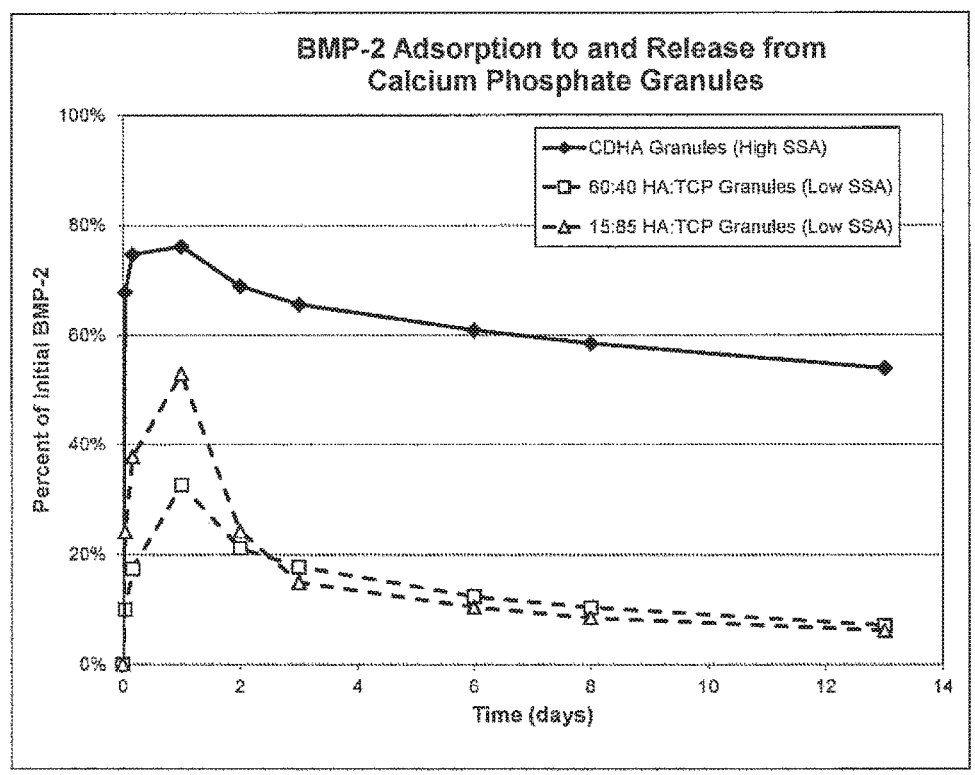
FIG. 3 shows in vitro loading/retention profiles (on/off rate) for BMP-2 delivered on a calcium deficient hydroxyapatite granule (CDHA) with high specific surface area compared to two BCP granules with low specific surface area. BMP was loaded onto the CaP granules in BMP buffer solution over a 24 hours period. The BMP-loaded CaP granules were then incubated in a solution containing 20% bovine serum to mimic exposure to serum proteins in vivo. High specific surface area CDHA granules loaded BMP-2 more efficiently compared to the low specific surface area BCP granules. In addition, more than 70% of the loaded BMP-2 remained bound to the granules over the subsequent 13-day period. In contrast, both low specific surface area BCP granules rapidly released a significant amount of BMP-2 in the first 24 hours and retained less than 20% of the initially loaded BMP-2 at 13 days.

CaP granules with specific surface area (SSA) in the range of 50-80 $m^2/g$ appear to have optimal in vitro BMP binding (FIGS. 3-6). High specific surface area likely increases binding by increasing the available surface area for binding of BMP to the CaP. High specific surface area CDHA granules loaded BMP-2 more rapidly and loaded a higher percentage of the available BMP-2 compared to the low specific surface area BCP granules (FIG. 3). In addition, more than 80% of the loaded BMP-2 remained bound to the granules over the subsequent 12-day period (FIG. 3). In contrast, both low specific surface area BCP granules rapidly released a significant amount of BMP-2 in the first 24 hours and retained less than 20% of the initially loaded BMP-2 at 13 days. Evaluating a large number of commercial granules with a wide range of specific surface areas confirmed this result.

Figure 4:
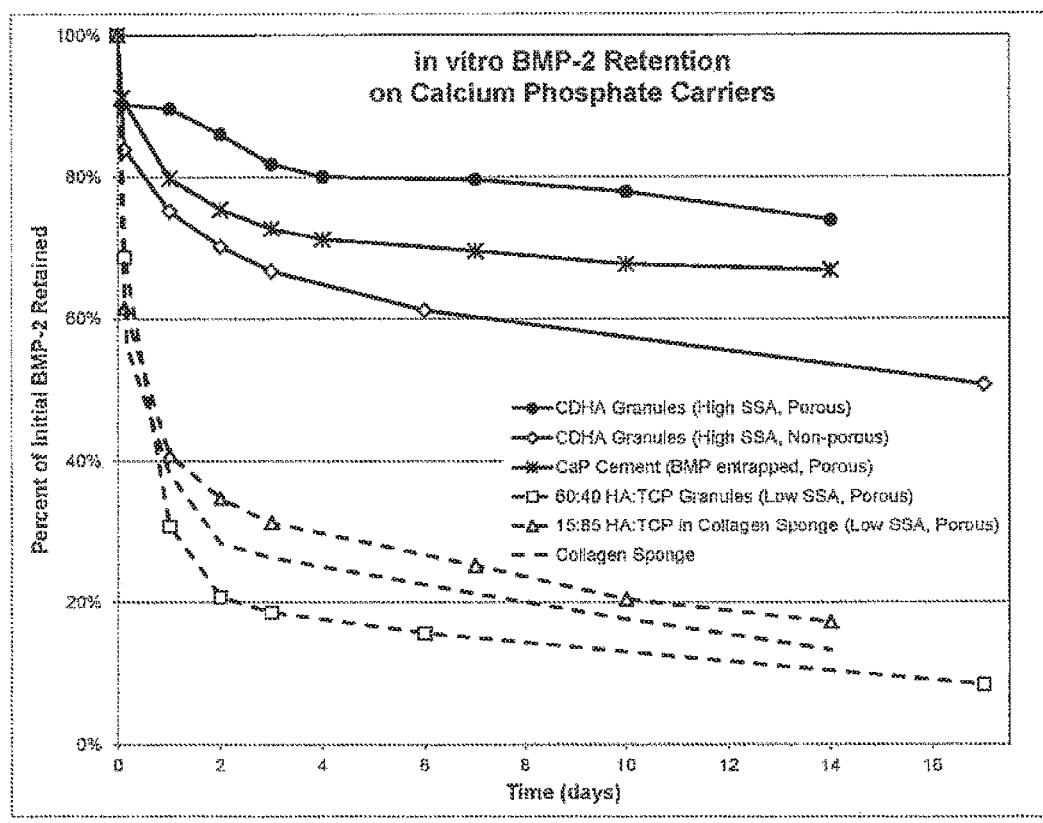
FIG. 4 shows the in vitro retention profile (% of initial) for BMP-2 delivered in CDHA porous high SSA (specific surface area) granules, CDHA non-porous high SSA granules, macroporous calcium phosphate cement (CaP), 60:40 HA/TCP porous granules, 15:85 HA/TCP porous granules compared to an absorbable collagen sponge (ACS) as a function of time in days. High specific surface area CDHA granules with and without porosity and CaP cements had superior BMP in vitro retention compared to ACS and low SSA granules either alone or contained within a collagen sponge.
Figure 5:
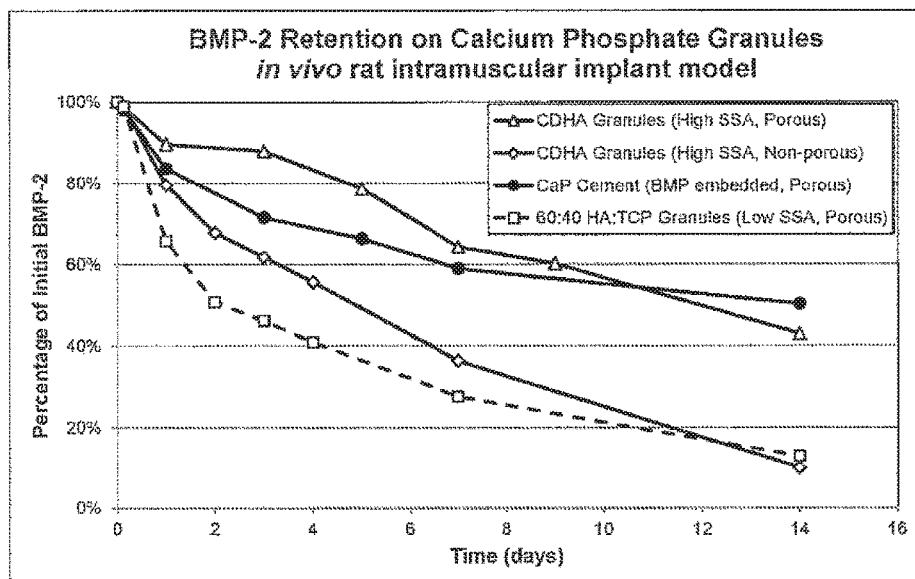
FIG. 5 shows the in vivo BMP-2 retention profiles using an intramuscular implant model in rats for high SSA CDHA granules with a microporous and macroporous structure compared to high SSA CDHA granules without an internal pore structure and low SSA 60:40 HA:TCP granules with a porous structure. Low SSA granules demonstrated the lowest BMP-2 retention, and high SSA granules without a porous structure demonstrated only a slightly improved BMP-2 retention profile. However, high SSA granules with a porous architecture demonstrated superior BMP-2 retention with 50% of the initial protein still remaining for at least 12 days. The BMP-2 retention profile of the high SSA granules with a porous structure is markedly similar to that of the CaP cement where the BMP is entrapped within the cement matrix.
Figure 6:
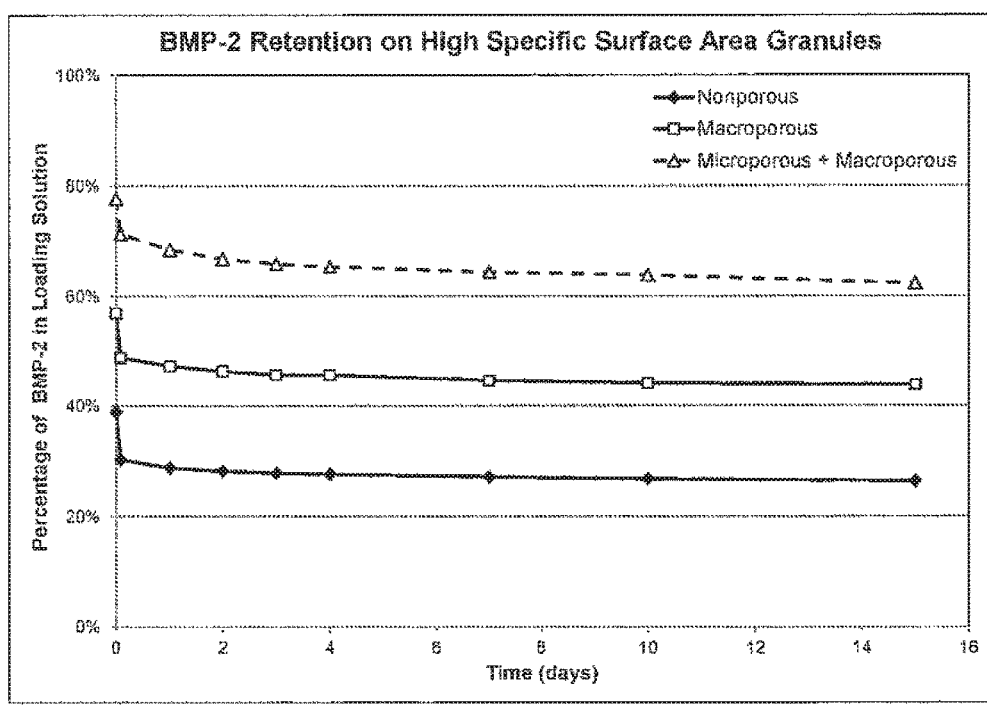
FIG. 6 shows the in vitro retention profiles for BMP-2 delivered in high specific surface area (SSA) Calcium Deficient Hydroxyapatite (CDHA) granules with microporous and macroporous internal architecture compared to high SSA CDHA granules with only macroporous internal architecture and high SSA CDHA granules without internal architecture as a function of time in days. High SSA CDHA granules with both microporous and macroporous internal architecture loaded the highest percentage of the available BMP. High SSA CDHA granules with macroporous internal architecture loaded an intermediate percentage of the available BMP. High SSA CDHA granules without internal architecture loaded the smallest percentage of available BMP. The subsequent retention profiles were similar for all three granule types.
Figure 7A:
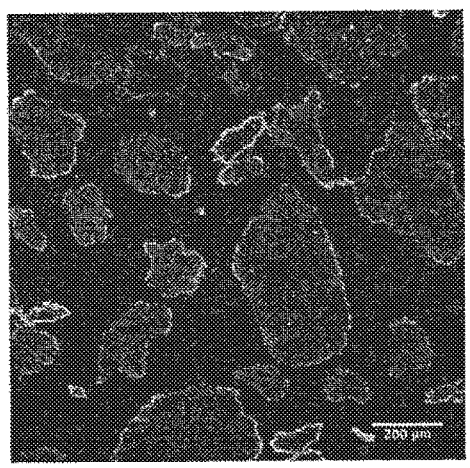
FIGS. 7A and 7B show photomicrographs of granules loaded with BMP-based osteoinductive proteins without (A) and with (B) loading buffers according to certain embodiments of the invention. 7A shows that when fluorescently labeled BMP is delivered in a weakly buffered solution, the protein is restricted to the surface of the ceramic granules. In contrast, when fluorescently labeled BMP is delivered in a well-buffered, low pH solution, the protein is able to penetrate and localize to the interior surfaces of the ceramic granules.
Figure 7B:
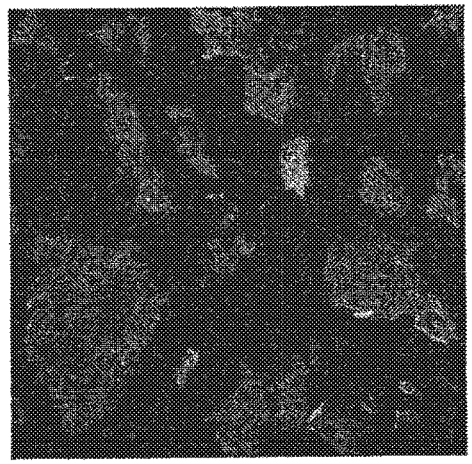

Interestingly, the addition of internal granule architecture (for instance, via the incorporation of micropores) also appears to further increase the rate of BMP-2 binding and the amount of BMP-2 bound particularly to larger CDHA granules with high specific surface area (FIGS. 4-6). The explanation for this phenomenon may be related to additional internal surfaces available for binding and the ability of granules with internal architecture to wick BMP containing fluid into the granules. This may be important if the external surfaces of granules without internal architecture become saturated with BMP or preferential BMP binding sites on external surfaces become saturated. Diffusion limitations of BMP-2 out of surfaces within the microporous structure compared to granules without internal architecture may also play a role in increasing the BMP retention profiles.

Additionally, internal architecture appears to be required for optimal in vivo BMP retention in CaP granules (FIG. 5). High SSA granules with sufficient internal architecture to allow BMP to penetrate inside the granules have superior in vivo BMP retention than high SSA granules without internal architecture. The optimal in vivo BMP retention is likely due to the specific dimensions of the internal architecture of the granules to conduct BMP solution inside the granules to allow BMP to bind to the internal surfaces of the granule while preventing osteoclasts from entering. As a result, osteoclasts have to resorb the majority of the granule from the outside in to release the internally bound BMP. This phenomenon mimics the optimal osteoclast mediated gradual release of BMP from CaP cements.

The internal architecture of calcium ceramic granules of the present invention is defined, in many cases, by micropores. Micropore dimensions generally vary with the size of the particles themselves, but as a general matter, the micropores in calcium ceramic granules of the invention are sized to permit fluids, to flow or migrate deep into the particle before encountering a granule surface. Thus, when these granules are incubated in BMP-containing solutions, the BMP is able to penetrate and adhere to surfaces that are deep within the interior of the granule.

The design criteria for the geometry of the internal granule architecture required to allow optimal BMP retention are complex. Micropores on the order of 2-10 um are required to allow BMP in solution to penetrate into the granules without immediately contacting the CaP surfaces on the outside of the granules. This is required as a result of the high binding affinity of BMP for CaP, particularly with high specific surface area. These types of surfaces have an extremely high carrying capacity to bind BMP. Without wishing to be bound by theory, it is thought that without the appropriate microporosity, the outside surfaces of the granules would filter out all the available BMP in solution preventing BMP penetration into the internal structure of the granules. This size range of micropores is also small enough to prevent multinucleated osteoclasts from penetrating into the inside of the granules. For granules with a diameter larger than about 200 um, larger secondary macropores on the order of 20-50 um are required to conduct the BMP solution further into the interior of the granules. In preferred embodiments, macro- and micropores form a network of interconnected passageways through which fluid can penetrate into a granule. It should be noted, however, that internal architecture is not sufficient for optimal BMP retention for granules that have low specific surface area.

Solutions and Kits for Protein Loading of Granules

In constructs of the present invention, BMPs are primarily carried by the ceramic granules embedded within the construct. However, as discussed above, current methods for loading granules with BMP result in BMP accumulation on the exterior surfaces of the granules, creating a protein "rim" rather than penetrating the highly porous structures of the granules that are described above. The protein rim may contribute to burst release of BMP following construct implantation, while penetration of BMP into the granules may contribute to an extended release profile insofar as BMP associated with internal surfaces of the granules are shielded from release until the implanted granules degrade, for example due to osteoclastic activity at the site of implantation. Without wishing to be bound by any theory, it is believed that, in general, BMPs are highly soluble in low pH, low-ionic strength buffers; state of the art BMP buffers with these characteristics generally have low buffering capacities. On the other hand, CaP granules are generally alkaline; this difference may contribute to the relatively limited infiltration of BMP into granules using current methods.

The inventors have discovered two factors that facilitate the penetration of BMP into the interior pore structure of the granules: first, the inventors have found that pre-treatment of the granules with an acid solution (for example, 50 mM hydrochloric acid (HCl) or, more preferably, 500 mM acetic acid), also referred to as "etching" the granules, prior to incubation of the granules (either alone or incorporated into constructs) with BMP-containing solutions (referred to as the "protein loading" step) aids in the transport of BMP into the interior pore structure of the granules. An alternative strategy to achieve a similar result is to manufacture the granules in such a way that the final pH of the granules remains below pH 7, more preferably at or below pH 6. Second, the inventors have found that certain compositions, including generally those with relatively higher buffering capacities, also facilitate transport of BMP into the interior pores of the granules. Each of these factors is discussed in turn below:

With respect to etching of granules prior to protein loading, the inventors have found that pre-treatment of the granules by 15 minute-4 hour incubation in an acidic solution, preferably 500 mM acetic acid, at a ratio of 10 mL per gram weight of calcium-deficient hydroxyapatite (CDHA) granules improves infiltration of the BMP into the granules. Treating granules with acid lowers the pH of the granules to pH 5.5-6.0. pH of granules is measured according to a standardized protocol, in which 0.25 grams of granules are mixed with 12.5 mL of a solution comprising 1% NaCl, then a pH measurement is made from the resulting slurry.

Etching can also result, in certain cases when the buffer is of sufficiently high buffer capacity and sufficiently low pH, in increased release of BMP into solution, e.g. during washing of the granules. The skilled artisan will appreciate, additionally, that protein loading and elution results similar to those obtained by etching of granules may be obtained in some instances by utilizing granules having an inherently low (e.g. less than 7.0) pH in their as-manufactured state.

With respect to new BMP buffers, the inventors have found that several buffer components and/or compositions can result in improved infiltration of BMPs into the internal pores of granules. A non-limiting listing of buffers according to the present invention (as well as the clinically used rhBMP-2 buffers for purposes of comparison) appears in Table 2:

TABLE 2
EXEMPLARY BUFFER COMPOSITIONS

| Buffer | Composition | pH |
|---|---|---|
| BVB-001 Buffer | • 5 mM Glutamic Acid<br>• 0.15% Glycine<br>• 1% Sucrose<br>• 0.01% Polysorbate-80 (OPTIONAL)<br>• Water for Injection | 4 |
| BVB-005 Buffer | • 25 mM Glutamic Acid<br>• 0.75% Glycine<br>• 1% Sucrose<br>• 0.01% Polysorbate-80 (OPTIONAL)<br>• Water for Injection | 3.5 |
| BVB-010 Buffer | • 50 mM Glutamic Acid<br>• 1.5% Glycine<br>• 1% Sucrose<br>• 0.01% Polysorbate-80 (OPTIONAL)<br>• Water for Injection<br>• pH Adjusted with HCl | 3 |
| BVB-012 Buffer | • 25 mM Glutamic Acid<br>• 2% Glycine<br>• 1% Sucrose<br>• Water for Injection | 4 |
| BMP2 buffer-1 | • 5 mM Glutamic Acid<br>• 2.5% Glycine<br>• 0.5% Sucrose<br>• 5 mM NaCl<br>• 0.01% Polysorbate-80<br>• Water for Injection | 4.5 |
| BMP2 buffer-2 | • 25 mM Glutamic Acid<br>• 2.5% Glycine<br>• 0.5% Sucrose<br>• 2 mM NaCl<br>• 0.01% Polysorbate 80<br>• Water for Injection | 4.5 |

The inventors have found that the BVB-005 ("5×") and BVB-010 ("10×") buffer formulations improve BMP infiltration into granules relative to the BMP-2 buffers used previously or the relatively weak buffer BVB-001 ("1×"). More generally, and without wishing to be bound by any theory, weakly acidic buffer solutions with buffering capacities sufficient to maintain low pH (e.g. less than 5.0) when incubated with granules are preferred in various embodiments of the present invention. Specifically, while the solutions set forth in Table 2 are buffered by glutamic acid and/or glycine, a variety of other buffering agents are useful in protein loading solutions of the present invention, including lactic acid, acetic acid, formic acid, malic acid, malonic acid, aspartic acid, citric acid, tartaric acid, phosphoric acid, fumaric acid and/or succinic acid. In preferred cases, the buffering agent has a pKa between about 2.3 and 4.5, while the buffer as a whole preferably has a pH between 3.5 and 4.0.

In addition to buffering agents, solutions of the present invention can optionally incorporate one or more additives, including without limitation 0.01%-0.1% (w/v) polysorbate-80, 0.5%-5% (w/v) Sucrose, 0.5%-5% (w/v) Trehalose, 0.5%-5% (w/v) Sorbitol or 0.5%-5% (w/v) Mannitol.

By way of example (and not limitation), one buffer solution according to the present invention has a composition of (i.e. consists essentially of) 5 mM Glutamic acid, 0.15% (w/v) Glycine, 1% Sucrose, and water with a pH of 4.0. Another buffer solution is 50 mM Glutamic acid, 1.5% (w/v) Glycine, 1% Sucrose, and water with a pH adjusted to 3.0 with hydrochloric acid, and another suitable buffer is 50 mM Glutamic acid, 0.75% (w/v) Glycine, 1% Sucrose, and water with a pH of 3.5. Yet another buffer solution is 25 mM Glutamic acid, 0.75% (w/v) Glycine, 1% Sucrose, and water with a pH adjusted to 3.5 with HCl, another is 25 mM Glutamic acid, 0.75% (w/v) Glycine, 1% Sucrose, and water with a pH of 3.7, and another buffer solution is 25 mM Glutamic acid, 2% (w/v) Glycine, 1% Sucrose, and water with a pH of 4.0. Still another suitable buffer solution is 50 mM Glutamic acid, 1.5% (w/v) Glycine, 1% Sucrose, and water with a pH of 3.7. Other buffer solutions may have similar compositions with the inclusion of additional or modified components.

Figures 8A, 8B, 8C, 8D, 8E, 8F:
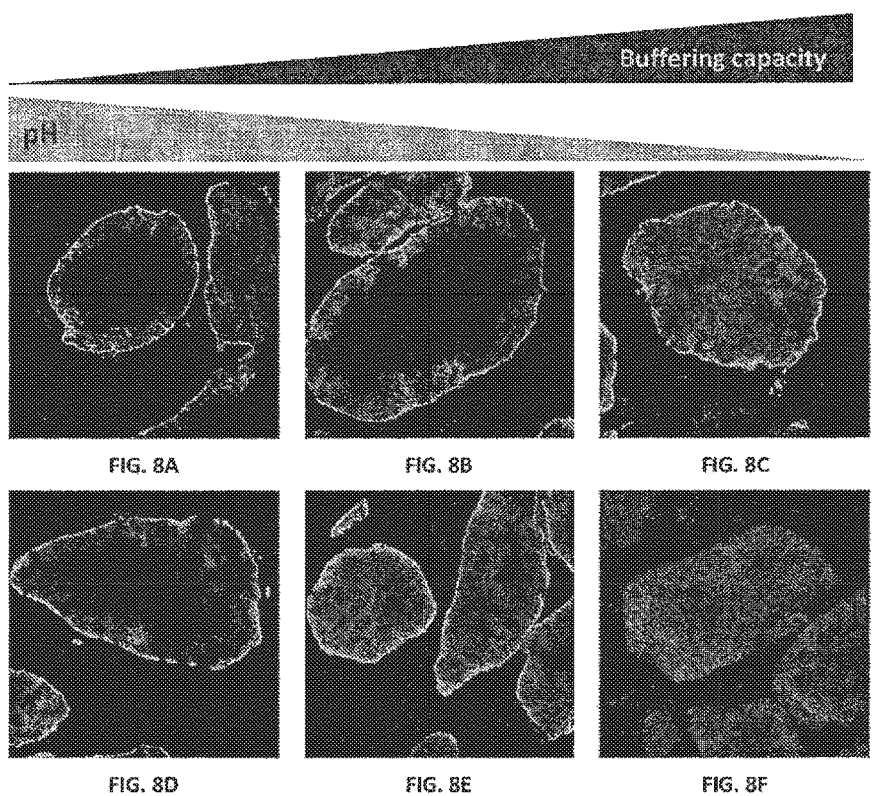
FIGS. 8A through 8F shows micrographs of untreated (A-C) and acid pre-treated ("etched") (D-F) granules loaded with fluorescently labeled BMP in varying buffer compositions. In the first column (A&D), granules were loaded with protein in a low buffering capacity pH 4.0 buffer ("BVB-001 Buffer"; for composition see Table 2). In the second column (B&E), the granules were loaded with protein in an intermediate buffering capacity pH 3.5 buffer ("BVB-005 Buffer"). In the third column, the granules were loaded with protein in a high buffering capacity pH 3.0 buffer ("BVB-010 Buffer"). The distribution of protein shifts from being concentrated at the surface of the granules in A&D to a more uniform distribution as buffering capacity increases and pH decreases (i.e. the protein is distributed along pore surfaces near the centroid and near the exterior surface of the granules). The combination of etched granules and the BVB-010 buffer gave the most uniform distribution of protein.

FIG. 8 includes several fluorescent micrographs of naïve (panels A, B, C) and etched (panels E, F, G) granules treated with buffers having various pH and buffering capacities during the protein loading step. In naïve granules, a protein rim was visible in all conditions, and in both naïve and etched granules, infiltration of the granules improved as the buffering capacity and acidity of the buffer solution increased. Importantly, infiltration of BMP into granules was improved by etching when intermediate buffering capacity buffers were used (panels B and E), but good infiltration was also observed in naïve granules loaded in buffers with high-buffering capacity. These results indicate that it is not strictly necessary to pair high-buffering capacity, low pH protein loading buffers with granule etching to achieve good BMP infiltration into the granules; accordingly, various embodiments of the present invention utilize etching and/or the improved protein loading buffer. Again, the skilled artisan will appreciate, additionally, that protein distribution results similar to those obtained by etching of granules may be obtained in some instances by utilizing granules having an inherently low (e.g. less than 7.0) pH in their as-manufactured state.

Figure 10:
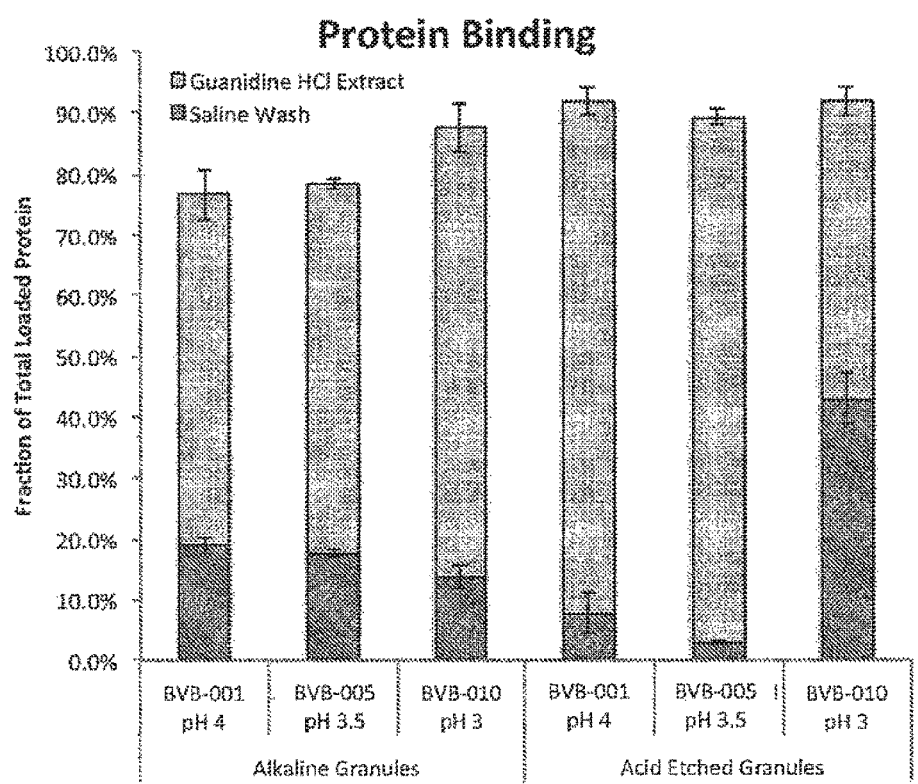
FIG. 10 illustrates the partitioning of the protein between a saline wash and a guanidine HCl extract following incubation of BMP with untreated or etched granules in varying buffer compositions. The protein in the saline wash is considered loosely bound to the granules, whereas the protein in the guanidine HCl extract is considered tightly bound to the granules. In untreated granules, the amount of loosely bound BMP decreases as the buffering capacity increases and the pH decreases (i.e., from "BVB-001" to the "BVB-010" buffer conditions). For etched granules a similar pattern was observed until the BMP was loaded in the high buffering capacity pH 3 buffer (BVB-010) in which case the fraction of loosely bound protein increased dramatically over that for the BVB-001 and BVB-005 conditions.
Figure 11:
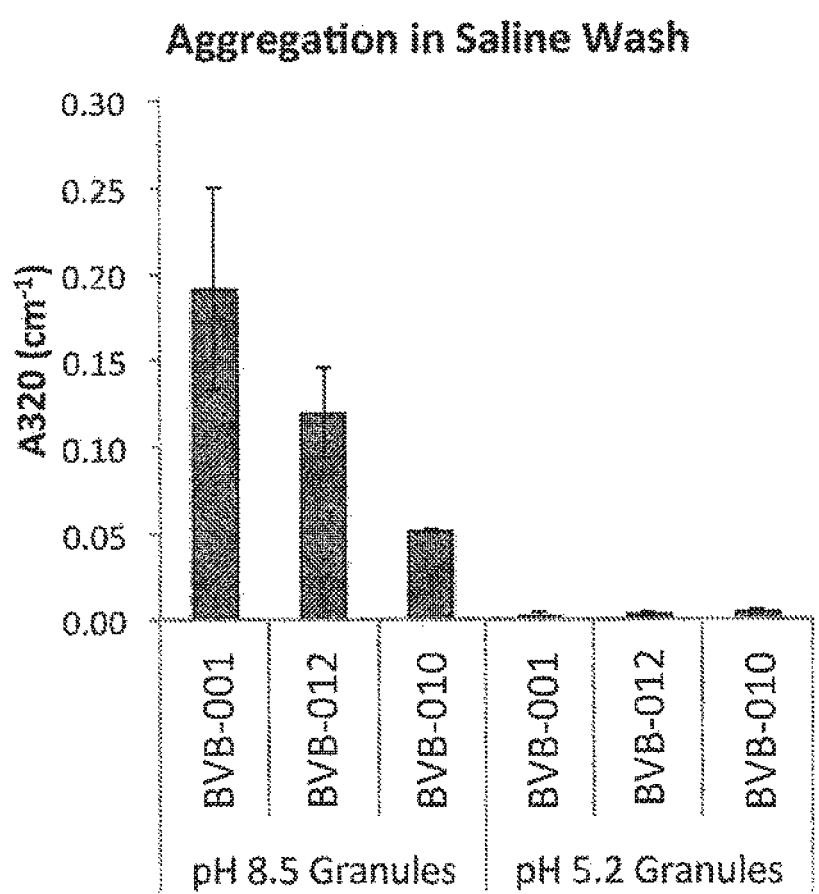
FIG. 11 shows that in alkaline granules (e.g. pH 8.5) the BMP tends to be aggregated (high A320 values) and the extent of aggregation generally decreases as the strength of the buffer increases (BVB-001→BVB-012→BVB-010 Buffers). Additionally, in low pH granules (e.g. pH 5.2) the BMP tends to be less aggregated overall, thereby better enabling delivery to the interior of the granules.
Figure 12A:
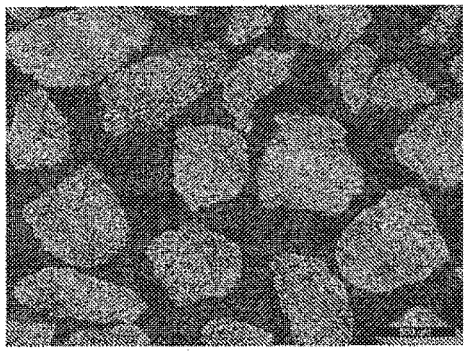
FIGS. 12A through 12D shows SEM pictures of the polished surfaces of a CDHA granule with complex internal architecture. The granule contains highly interconnected pores approximately 10 um in size. At the highest magnification individual CaP crystal spicules within the pores can be observed generating the high specific surface area characteristic of CDHA granules. The optimal in vivo BMP retention is likely due to BMP solution penetrating the microporous structure allowing BMP to bind to the internal CaP surfaces where it is protected from invading cell populations such as osteoclasts.
Figure 12B:
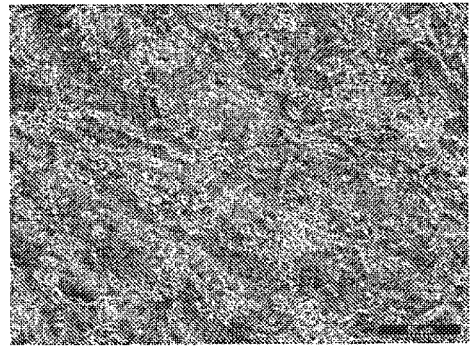
Figure 12C:
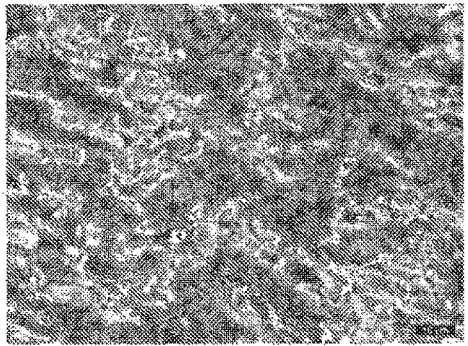
Figure 12D:
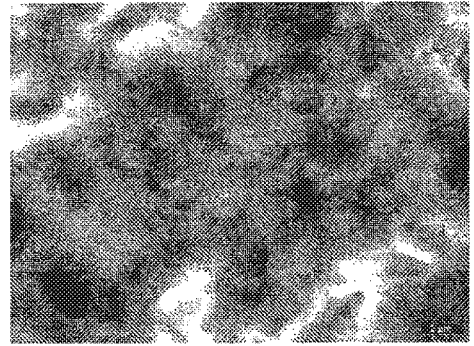
Figure 13A:
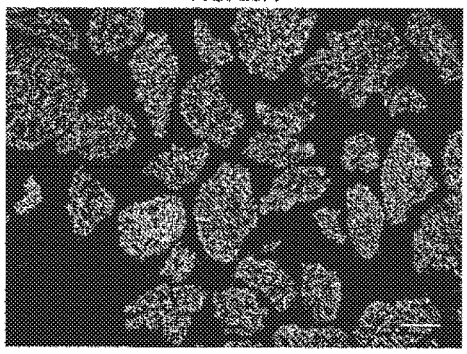
FIGS. 13A through 13D illustrate the physical and chemical characteristics of granules of the present invention and demonstrates that these properties enable the ability to deliver BMPs in vivo at a well-controlled rate.
Figure 13B:
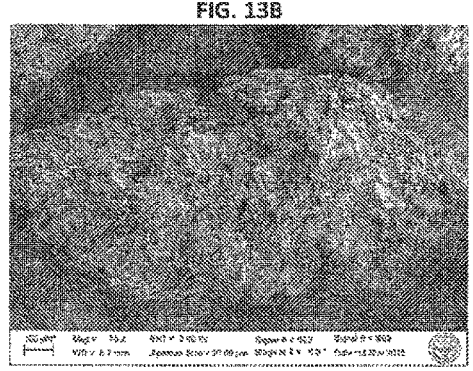
Figure 13C:
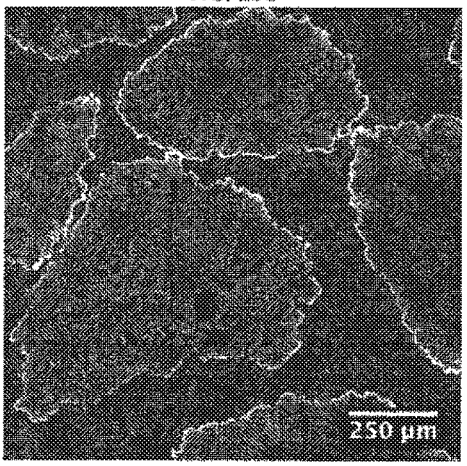
Figure 13D:
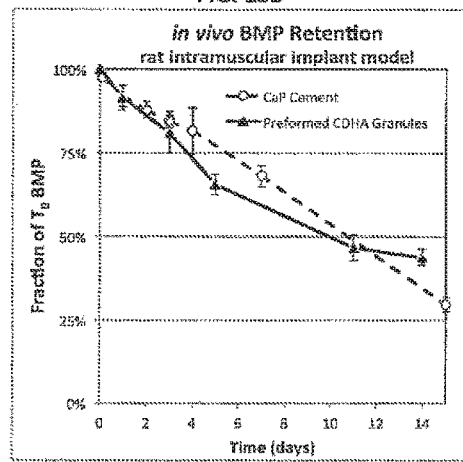

The inventors have also found, however, that different combinations of granule pH (e.g. etched treatment) and buffering solutions can result different degrees of apparent binding between the granules and BMP, as evidenced by the fraction of BMP eluted in a saline wash of the BMP loaded granules. FIG. 10 illustrates the BMP fractions eluted in the saline wash (dark bars) and a subsequent guanidinium chloride protein extraction (light bars). In general, about 20% or less of the BMP elutes during the saline wash, though in etched granules loaded with BVB-010 buffer almost 40% of the BMP eluted during the wash, while etched granules loaded with BVB-005 buffer released less than 10% of their BMP during the wash. Without wishing to be bound by any theory, it is believed that these differences may correlate with differences in BMP release by implanted constructs, and the present invention encompasses constructs with BMP release kinetics that can be tuned by varying the BMP loading buffer and/or the pH (etching) of the granules.

In use, protein-loaded granules generated through the use of the compositions and methods of the present invention form one part of a multipart construct for use in treating patients. As is described above, these constructs generally include an osteoinductive protein that is preferably associated with and elutes from granules with complex and interconnected networks of micropores of varying size, which granules are in turn embedded, inserted, or otherwise in contact with a polymer matrix that has a macroporous structure to facilitate cellular and vascular infiltration, and which is characterized by a residence time on the order of several weeks (advantageously permitting extended delivery of osteoinductive protein as more specifically described above) and a stiffness and compression resistance sufficient to enable the construct to remain intact and provide structural support for new bone growth when implanted. These constructs will typically include a porous polymer matrix preferably comprising collagen but, optionally comprising other naturally-occurring or synthetic polymers.

Granules (alone or integrated into constructs) can be bundled into kits that can include one or more of a BMP loading solution, an applicator for applying the loading solution to the granules or a granule-containing construct or composition, and/or for placing the construct in the body of a patient, and instructional materials which describe use of the kit, or its components, to perform the methods of the invention. Although exemplary kits are described herein, the contents of other useful kits will be apparent to the skilled artisan in light of the present disclosure. Each of these kits is included within the invention.

The invention includes a kit for treatment to prevent loss of and/or increase bone mass in a patient in need thereof. The kit includes a composition comprising granules as described above, along with an osteoinductive protein, which can be in lyophilized or other dry form or, more preferably in solution in a buffer described above. If the protein is lyophilized or otherwise not in solution, the kit also preferably include a diluent or loading buffer as described above. The kit also includes an applicator, including, but not limited to, a syringe for adding fluid to the protein vessel and/or wetting the granule-containing composition, or a delivery apparatus for placing the composition, including granules loaded with the osteoinductive protein, into the body of a patient. Further, the kit can optionally include an instructional material setting forth the pertinent information for the use of the kit to treat or prevent bone loss, promote union or knitting of a fracture, and/or otherwise increase bone mass or treat a bone condition in the patient.

Conclusion

Throughout this application, reference is made to "macropores," "micropores" and macro- and microporosity. In general, macropores have a cross-sectional dimension greater than 100 microns, while micropores are between 100 nm and 100 microns. Pores less than 100 nm are referred to as nanopores.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts of up to 2% or more in some instances.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A composition, comprising:
   a preformed calcium ceramic granule having a specific surface area greater than 30 $m^2/g$ and having an interconnected network of micropores defining at least one surface on an interior of the granule; and
   an amount of osteoinductive protein adsorbed to the exterior surface of the granule and adsorbed onto the at least one interior surface, wherein the osteoinductive protein is distributed on a portion of the interior surface of the granule including on a portion of the interior surface within a radius of 20% of the average distance from the centroid of the granule to the outer surface of the granule, wherein a concentration of osteoinductive protein adsorbed to said portion of the interior surface within a radius of 20% of the average distance from the centroid to the outer surface of the granule is not less than 33% of a concentration of the osteoinductive protein adsorbed to the external surface of the granule.

2. The composition of claim 1, further comprising a biocompatible matrix, wherein ceramic granules are disposed within the biocompatible matrix.

3. The composition of claim 2, wherein the biocompatible matrix is a sponge having a plurality of pores, the pores having an average diameter of about 150 to about 300 microns.

4. A composition, comprising:
a biocompatible porous polymer matrix;
a calcium ceramic granule contacting the porous polymer matrix, the calcium ceramic granule having a specific surface area greater than 30 $m^2/g$ and having an interconnected network of micropores defining at least one surface on an interior of the granule; and
an amount of an osteoinductive protein adsorbed onto the exterior surface and absorbed onto the at least one interior surface, wherein the osteoinductive protein is distributed on the interior surface including on a portion of the interior surface within a radius of 20% of the average distance from the centroid to the outer surface of the granule, wherein a concentration of osteoinductive protein adsorbed to said portion of the interior surface within a radius of 20% of the average distance from the centroid to the outer surface of the granule is not less than 33% of a concentration of the osteoinductive protein adsorbed to the external surface of the granule.

5. The composition of claim 4, wherein the ceramic granule is disposed within the biocompatible porous matrix.

6. The composition of claim 5, wherein the biocompatible porous matrix comprises collagen.

7. The composition of claim 5, wherein the biocompatible matrix is a sponge having a plurality of pores, the pores having an average diameter of about 150 to about 300 microns.

8. The composition of claim 4, wherein the osteoinductive protein is adsorbed to the at least one interior surface of the granule by a method including the step of contacting the granule with a first solution comprising the osteoinductive protein and a buffering agent having a pKa between 2.3 and 4.5, the solution having a pH less than 4.5.

9. A method of treating a patient, comprising the steps of:
contacting a bony tissue of the patient with a composition, comprising:
a calcium ceramic granule having a specific surface area greater than 30 $m^2/g$ and having an interconnected network of micropores defining at least one surface on an interior of the granule; and
an amount of osteoinductive protein adsorbed to an exterior surface of the granule and adsorbed onto the at least one interior surface, wherein the osteoinductive protein is distributed on a portion of the interior surface of the granule including on a portion of the interior surface within a radius of 20% of the average distance from the centroid to the outer surface of the granule, wherein a concentration of osteoinductive protein adsorbed to said portion of the interior surface within a radius of 20% of the average distance from the centroid to the outer surface of the granule is not less than 33% of a concentration of the osteoinductive protein adsorbed to the external surface of the granule.

10. The method of claim 9, wherein the bony tissue is selected from the group consisting of a site of a traumatic injury to the bone and a vertebra.

11. The method of claim 9, wherein the composition includes a biocompatible matrix, the ceramic granule disposed within the biocompatible matrix.

12. The method of claim 11, wherein the biocompatible matrix comprises collagen.

* * * * *